United States Patent
Tamura et al.

(10) Patent No.: US 10,031,999 B2
(45) Date of Patent: Jul. 24, 2018

(54) INFORMATION PROCESSING APPARATUS FOR DETERMINING REGISTERED USERS IN A SYSTEM

(71) Applicant: Sony Computer Entertainment Inc., Tokyo (JP)

(72) Inventors: Keigo Tamura, Tokyo (JP); Tomohiro Ogawa, Kanagawa (JP); Akitsugu Tsuchiya, Kanagawa (JP); Toshimasa Aoki, Kanagawa (JP)

(73) Assignee: Sony Interactive Entertainment Inc., Tokyo (JP)

( * ) Notice: Subject to any disclaimer, the term of this patent is extended or adjusted under 35 U.S.C. 154(b) by 481 days.

(21) Appl. No.: 14/437,138

(22) PCT Filed: Oct. 30, 2013

(86) PCT No.: PCT/JP2013/006413
§ 371 (c)(1),
(2) Date: Apr. 20, 2015

(87) PCT Pub. No.: WO2014/068968
PCT Pub. Date: May 8, 2014

(65) Prior Publication Data
US 2015/0254396 A1    Sep. 10, 2015

(30) Foreign Application Priority Data

Nov. 1, 2012  (JP) .................................. 2012-241760

(51) Int. Cl.
*A63F 9/24* (2006.01)
*G06F 19/10* (2011.01)
(Continued)

(52) U.S. Cl.
CPC .............. *G06F 19/10* (2013.01); *A63F 13/79* (2014.09); *G06F 21/31* (2013.01); *G06F 21/32* (2013.01);
(Continued)

(58) Field of Classification Search
None
See application file for complete search history.

(56) References Cited

U.S. PATENT DOCUMENTS 7,867,083 B2  1/2011  Uehlls
8,123,616 B2  2/2012  Uehlls
(Continued)

FOREIGN PATENT DOCUMENTS

CN        1804749 A      7/2006
CN      101169812 A      4/2008
(Continued)

OTHER PUBLICATIONS

Office Action for corresponding AU Patent Application 2013340071, 5 pages, dated Mar. 3, 2016.
(Continued)

*Primary Examiner* — Jason Yen
(74) *Attorney, Agent, or Firm* — Matthew B. Dernier, Esq

(57) ABSTRACT

A communication section receives a connection request from a game controller to connect the game controller with an information processing apparatus. A registered user information holding section holds biometric information of a user registered in the information processing apparatus. A biometric authentication portion compares biometric information of a user included in a taken image with biometric information held in the registered user information holding section to determine whether the imaged user is a user registered in the information processing apparatus. After the imaged user is found to be a user registered in the informa- (Continued)

tion processing apparatus, a login controller executes login processing of the user, or to be more specific, stores information for identifying a device included in the taken image and information for identifying the user into a login user storage portion by relating these items of information with each other.

8 Claims, 11 Drawing Sheets

(51) Int. Cl.
  *G06F 21/32* (2013.01)
  *A63F 13/79* (2014.01)
  *G06F 21/31* (2013.01)
  *G06F 21/35* (2013.01)
(52) U.S. Cl.
  CPC ........ *G06F 21/35* (2013.01); *A63F 2300/201* (2013.01); *G06F 2221/2109* (2013.01)

(56) References Cited

U.S. PATENT DOCUMENTS

| | | | |
|---|---|---|---|
| 8,295,549 B2 | 10/2012 | Marks et al. | |
| 2004/0062423 A1 | 4/2004 | Doi | |
| 2004/0192438 A1 | 9/2004 | Uehlls | |
| 2004/0192442 A1 | 9/2004 | Uehlls | |
| 2006/0076404 A1 | 4/2006 | Frerking | |
| 2007/0140145 A1* | 6/2007 | Kumar | G06F 21/32 370/254 |
| 2008/0115208 A1 | 5/2008 | Li | |
| 2008/0309617 A1* | 12/2008 | Kong | G06F 3/04817 345/157 |
| 2009/0138805 A1* | 5/2009 | Hildreth | G06K 9/00335 715/745 |
| 2009/0174657 A1 | 7/2009 | Miyazaki | |
| 2010/0169659 A1 | 7/2010 | Shnowske | |
| 2011/0092280 A1 | 4/2011 | Koyama | |
| 2011/0306419 A1 | 12/2011 | Miyazaki | |
| 2012/0257797 A1* | 10/2012 | Leyvand | G06K 9/00221 382/118 |
| 2012/0268360 A1 | 10/2012 | Mikhailov et al. | |
| 2013/0291093 A1* | 10/2013 | Matsuoka | H04L 9/3231 726/19 |
| 2013/0305324 A1* | 11/2013 | Alford, Jr. | G06F 21/31 726/5 |

FOREIGN PATENT DOCUMENTS

| | | |
|---|---|---|
| GB | 2342744 A | 4/2000 |
| JP | 2000122975 A | 4/2000 |
| JP | 2004118627 A | 4/2004 |
| JP | 2010-072688 A | 4/2010 |
| JP | 2012190443 A | 10/2012 |
| RU | 2338258 C2 | 11/2008 |
| RU | 2347274 C2 | 2/2009 |
| WO | 2007116578 A1 | 10/2007 |
| WO | 2011109742 A1 | 9/2011 |

OTHER PUBLICATIONS

European Search Report for corresponding EP 13851114, 11 pages, dated May 24, 2016.
Maria Langer: "Mac OS X 10.6 Snow Leopard: Visual QuickStart Guide" In: "MAC OS X 10.6 Snow Leopard : [learn MAC OS X the quick and easy way!]", Peachpit Press, Berkeley, Calif., XP055271640, ISBN: 978-0-321-63539-6 p. 297, 2 pages, (Dec. 31, 2010).
Office Action for corresponding RU Application No. 2015120656, 12 pages, dated Jan. 11, 2017.
Office Action for corresponding CN Application No. 201380055711.2, 11 pages, dated Oct. 9, 2016.
Office Action for corresponding JP Patent Application JP2012241760, pp. 1-5, dated Jan. 26, 2016.
International Search Report for corresponding application PCT/JP2013/006413, dated Jan. 28, 2015.
International Preliminary Report on Patentability and Written Opinion for corresponding PCT Application PCT/JP2013/006413, 7 pages, dated May 14, 2015.

* cited by examiner

FIG. 7
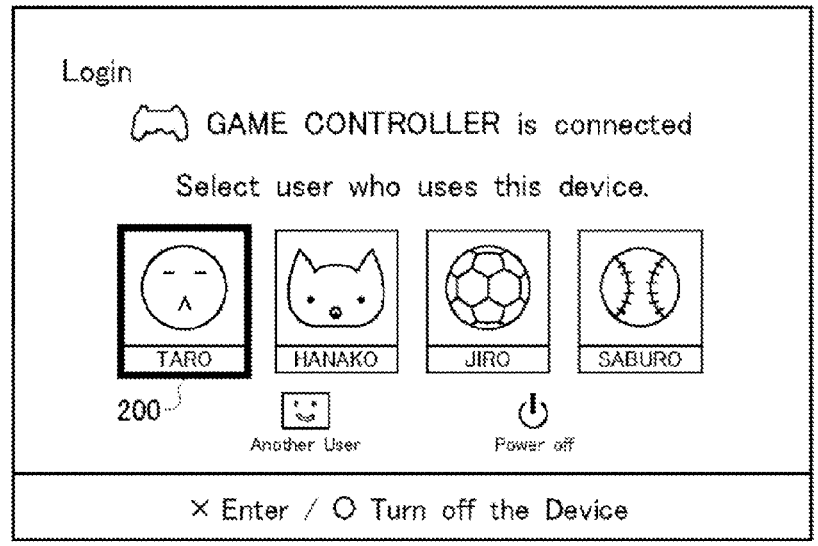
(a)
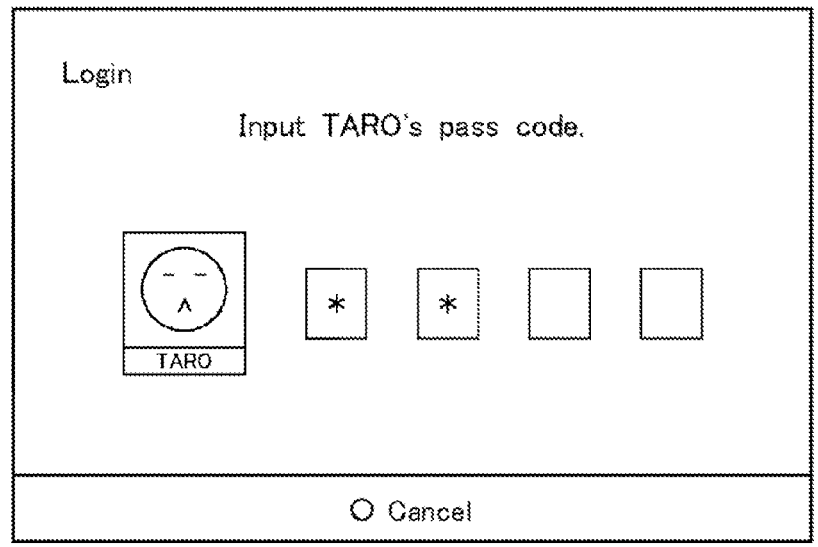
(b)

INFORMATION PROCESSING APPARATUS FOR DETERMINING REGISTERED USERS IN A SYSTEM

TECHNICAL FIELD

The present invention relates to an information processing apparatus such as a game machine.

BACKGROUND ART

There has been proposed a system which, when a user has achieved a mission set in a video game, grants the user a trophy as a virtual prize for the mission accomplished (see PTL 1). The trophies won by the user on the game machine are also registered in a server connected to a network so that trophy acquisition information is synchronized between the game machine and the server.

CITATION LIST

Patent Literature

[PTL 1] U.S. Patent Application Publication No. 2011/0092280

SUMMARY

Technical Problem

With a game device cited in PTL 1, only one user is able to log in on the operating system (OS) of the game device, so that users who are able to sign in on the server is limited to the user who has logged in on the OS. Hence, if a game is played by two or more persons, no users other than a login user can get trophies, leaving a room for improvement. It is therefore desirable to allow two or more users to log in on the OS of a game device, thereby granting a trophy to each user.

In order to achieve the above-mentioned objective, it is desirable to provide a mechanism that allows users to log in on the OS of each game device in a simple manner. It is also desirable that a mechanism for easy login is applicable not only to the login of game devices but also to the login of other types of information processing apparatuses. In addition, it is desirable to provide the simplicity of login not only for the case where two or more persons log in but also for the case where only one user logs in.

It is therefore one objective of the present invention to provide a technology that allows easy user login.

Solution to Problem

In order to solve problems described above, there is provided an information processing apparatus as one embodiment of the present invention. This information processing apparatus has a communication section configured to receive a connection request from a device to connect the device with the information processing apparatus; an image capture section configured to capture a taken image from an imaging apparatus; a registered user information holding section configured to hold biometric information of a user registered in the information processing apparatus; a biometric authentication portion configured to compare biometric information of a user included in the taken image with biometric information held in the registered user information holding section to determine whether the imaged user is a user registered in the information processing apparatus; and a login controller configured, after the imaged user is found to be a user registered in the information processing apparatus, to execute login processing of the user. The login control unit stores information for identifying a device included in a taken image and information for identifying a user of the device into a storage portion by relating these pieces of information with each other.

Another embodiment of the present information is also an information processing apparatus. This information processing apparatus has an image capture section configured to capture a taken image from an imaging apparatus; a registered user information holding section configured to hold information of a user registered in the information processing apparatus; a receiving section configured to receive a login request from a user; a first image generating block configured, if the receiving section receives a first login request, to display, on a display as a first login screen, a select image that allows the user to select information for identifying himself from among pieces of information for identifying a plurality of registered users arranged in a row, the pieces of information being held in the registered user information holding section; and a second image generating block configured, if the receiving section receives a second login request, to display the taken image on a display as a second login screen.

Incidentally, if other combinations of the above-outlined composing elements or the above expressions of the present invention are converted between different forms such as a method, a device, a system, a recording medium, and a computer program, they still constitute effective embodiments of this invention.

BRIEF DESCRIPTION OF DRAWINGS

FIG. 7(a) is a diagram illustrating one example of a select screen and (b) is a diagram illustrating one example of a pass code input screen.

DESCRIPTION OF EMBODIMENT

Figure 1:
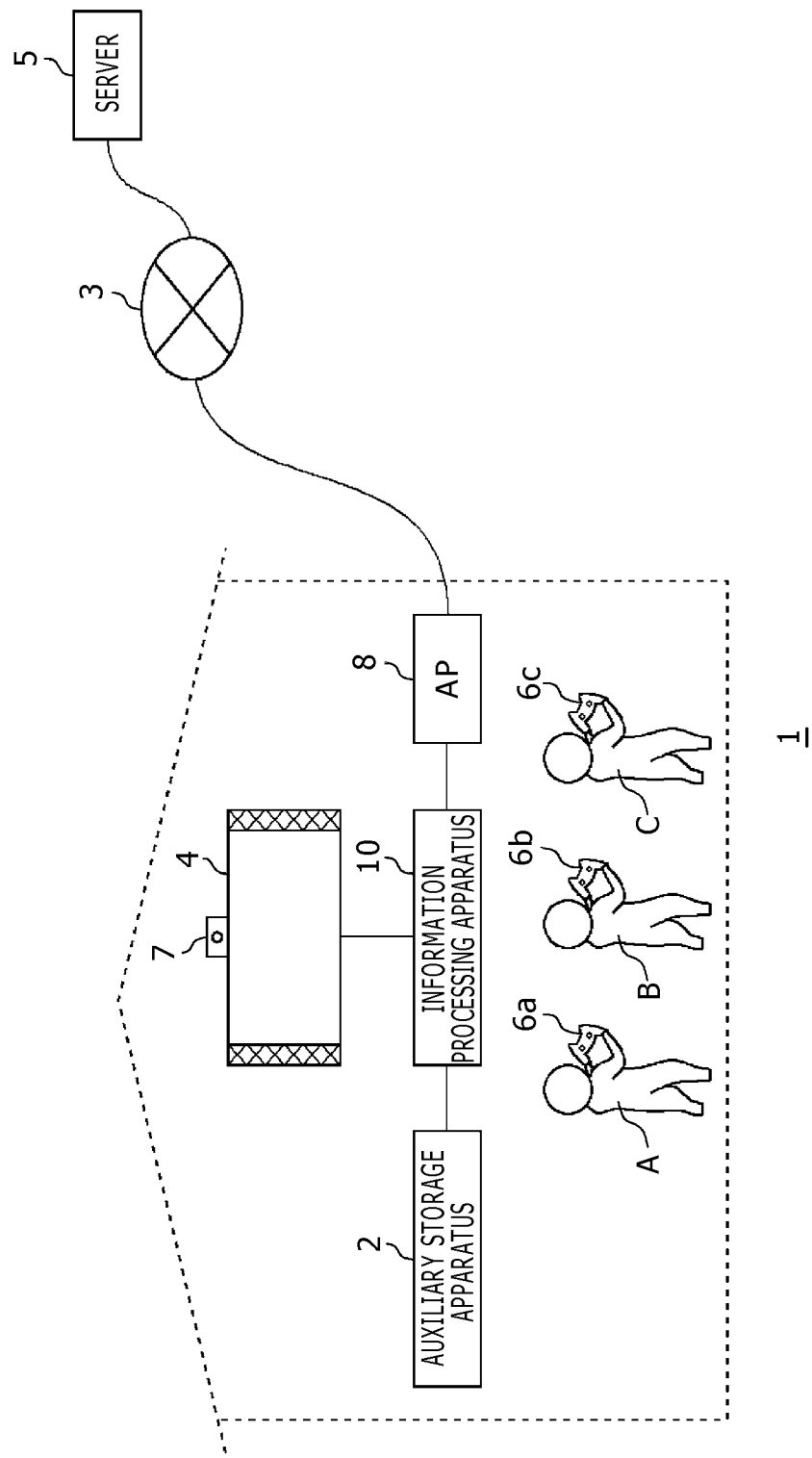
FIG. 1 is diagram illustrating an information processing system practiced as one embodiment of the present invention.

Now, referring to FIG. 1, there is shown an information processing system 1 practiced as one embodiment of the present invention. The information processing system 1 has an information processing apparatus 10 that is a user terminal and a server 5. An auxiliary storage apparatus 2 is a mass storage apparatus such as an HDD (Hard Disk Drive) or a flash memory, which may be an external storage apparatus connected to the information processing apparatus 10 through USB (Universal Serial Bus) or a built-in storage apparatus. An output device 4 may be a television set having a display for outputting images and a speaker for outputting audio or may be a computer display. The output device 4 may be connected to the information processing apparatus 10 with a wired cable or in a wireless manner. The information processing apparatus 10 is connected in a wired or wireless manner to an input device 6 that is operated by a user, the input device 6 outputting operation signals indicative of results of user operations to the information processing apparatus 10. Receiving operation signals from the input device 6, the information processing apparatus 10 reflects the received operation signals onto the processing of an application and output processing results from the output device 4. The input device 6 is configured by two or more input units such as two or more push-type operation buttons, an analog stick for entering analog quantity, and a rotary button. In the information processing system 1, the information processing apparatus 10 is a game device for executing a game and the input device 6 may be a device for providing user operation information to the information processing apparatus 10 such as a game controller. A camera 7 that is an imaging apparatus is arranged in the proximity of the output device 4 to take images of the spaces around the output device 4. In FIG. 1, the camera 7 is exemplarily mounted on top of the output device 4; however, the camera 7 may be arranged on one side of the output device 4. In any case, the camera 7 is arranged at a position where a user playing a game in front of the output device 4 can be taken.

An access point (hereafter referred to as "AP") 8 has the functions of a wireless access point and a router. The information processing apparatus 10 is connected to the AP 8 in a wireless or wired manner, thereby being communicably connected to the server 5 on a network 3.

The server 5 provides network services to users of the information processing system 1. The server 5 manages network accounts for user identification, and each user uses his or her account to sign in on network services provided by the server 5. By signing in on a network service from the information processing apparatus 10, each user is able to register in the server 5 game save data and trophies won during playing of a game. In addition, in the information processing system 1 of this embodiment, two or more users operating different information processing apparatuses 10 may take part in an online game. The server 5 may function as a game server for managing game sessions.

In FIG. 1, the server 5 may be represented as a server that consolidates the above-mentioned functions. Therefore, the server 5 may be physically configured by two or more servers and each of these servers may be maintained and managed by the entity according to each function.

In FIG. 1, three users A, B, and C are playing a game by use of the same information processing apparatus 10. Each user is logged in on the OS of the information processing apparatus 10 and is able to store save data in the information processing apparatus 10 and get trophies every time the user has achieved missions in the game. When each user logs in, the OS associates the user with the device (the input device 6). In this example, the OS associates an input device 6a with the user A, an input device 6b with the user B, and an input device 6c with the user C. Therefore, the game can identify the users from the information (game controller IDs for example) for identifying the input device 6.

Figure 2:
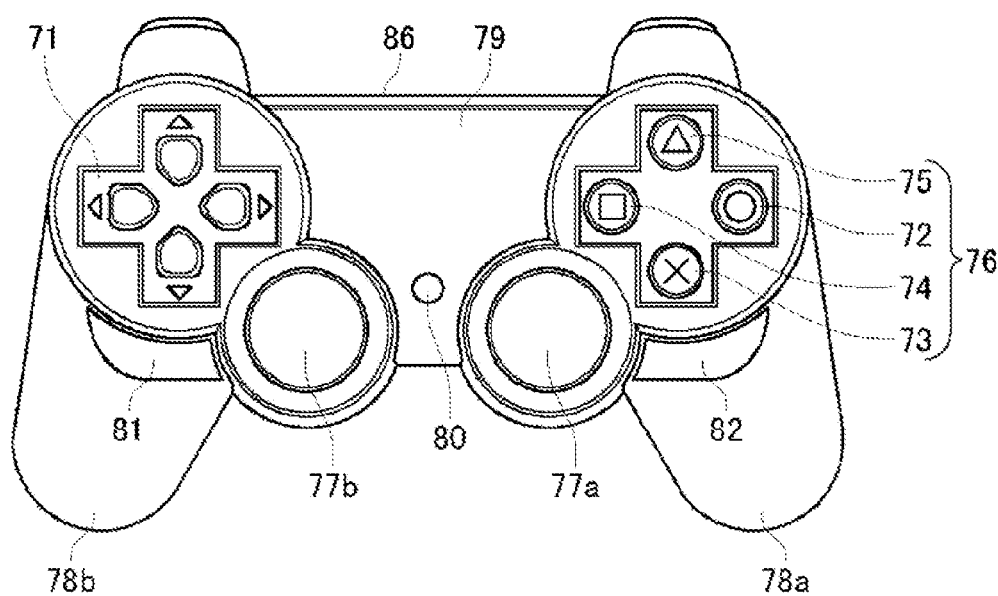
FIG. 2 is a diagram illustrating an external configuration of an input apparatus.

Referring to FIG. 2, there is shown an external configuration of the input device 6. A user holds a left-side grip 78b by the left hand and a right-side grip 78a by the right hand, thereby operating the input device 6. On a top housing surface 79 of the input device 6, a direction key 71, an analog sticks 77a and 77b, and four types of operation buttons 76 as input units are arranged. Four types of buttons 72 through 75 are marked with different symbols of different colors for discrimination from each other. Namely, the circle button 72 is marked with a red circle, the X button 73 is marked with a blue X, the square button 74 is marked with a violet square, and the triangle button 75 is marked with a green triangle. On the top housing surface 79, a flat area between the direction key 71 and the operation buttons 76 may have a touch pad.

Between the two analog sticks 77a and 77b, a function button 80 is arranged. The function button 80 is used to turn on the power to the input device 6 to activate the communication function for simultaneously connecting the input device 6 and the information processing apparatus 10. It should be noted that, if the main power to the information processing apparatus 10 is off, then, when the function button 80 is pressed, the information processing apparatus 10 receives a connection request transmitted from the input device 6 as an instruction for turning on the main power, upon which the main power to the information processing apparatus 10 is turned on. After the connection of the input device 6 to the information processing apparatus 10, the function button 80 is used also to display a menu screen on the information processing apparatus 10.

A SHARE button 81 is arranged on the left side of the left-side analog stick 77b. The SHARE button 81 is used to enter instructions from the user into the OS or system software in the information processing apparatus 10. In addition, an OPTION button 82 is arranged on the right side of the right-side analog stick 77a. The OPTION button 82 is used to enter instructions from the user into an application (a game) that is executed in the information processing apparatus 10. The SHARE button 81 and the OPTION button 82 may be formed as push buttons.

Figure 3:
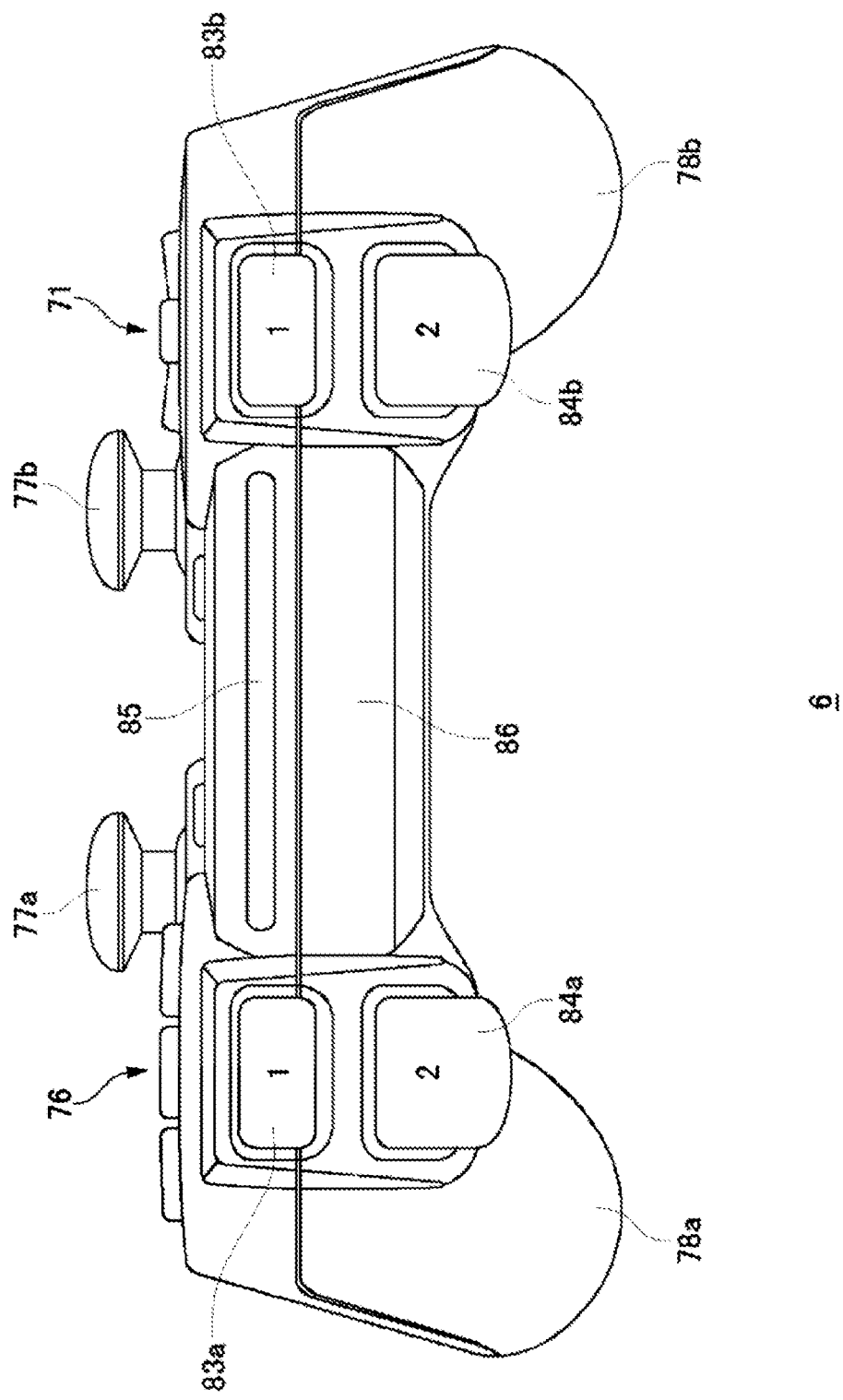
FIG. 3 is a diagram illustrating an external configuration of the rear side of the input apparatus.

Referring to FIG. 3, there is shown an external configuration of the rear side of the input device 6. On a housing rear surface 86 of the input device 6, a wide rather than long, approximately rectangular light-emitting block 85 is arranged. The light-emitting block 85 has red (R), green (G), and blue (B) LEDs, which are turned on in accordance with light-emitting color information transmitted from the information processing apparatus 10. A shown in FIG. 1, when three input devices 6a, 6b, and 6c are used, the information processing apparatus 10 may define the turn-on colors of the light-emitting blocks 85 of the input devices 6a, 6b, and 6c in different colors, namely, red, green, and blue, respectively, in order to allow the users A, B, and C to discriminate the input devices 6. Consequently, each user is able to recognize the input device 6 used by him or her by the turn-on color of the light-emitting block 85, thereby reducing the possibility of using a wrong input device 6.

On the housing rear surface 86, an upper button 83a, a lower button 84a, an upper button 83b, and a lower button 84b are arranged at symmetrical positions in the length direction. The upper button 83a and the lower button 84a are operated by the index finger and the middle finger, respectively, of the right hand of the user and the upper button 83b and the lower button 84b are operated by the index finger and the middle finger, respectively, of the left hand of the user. As shown, the arrangement of the light-emitting block 85 between the row of the right-side upper button 83a and the lower button 84a and the row of left-side upper button 83b and the lower button 84b avoids the hindrance by the index finger and the middle finger, thereby allowing the camera 7 to suitably taking an image of the turned-on light-emitting block 85. The upper buttons 83 may be formed as push buttons and the lower buttons 84 as trigger buttons which are turnably supported.

Figure 4:
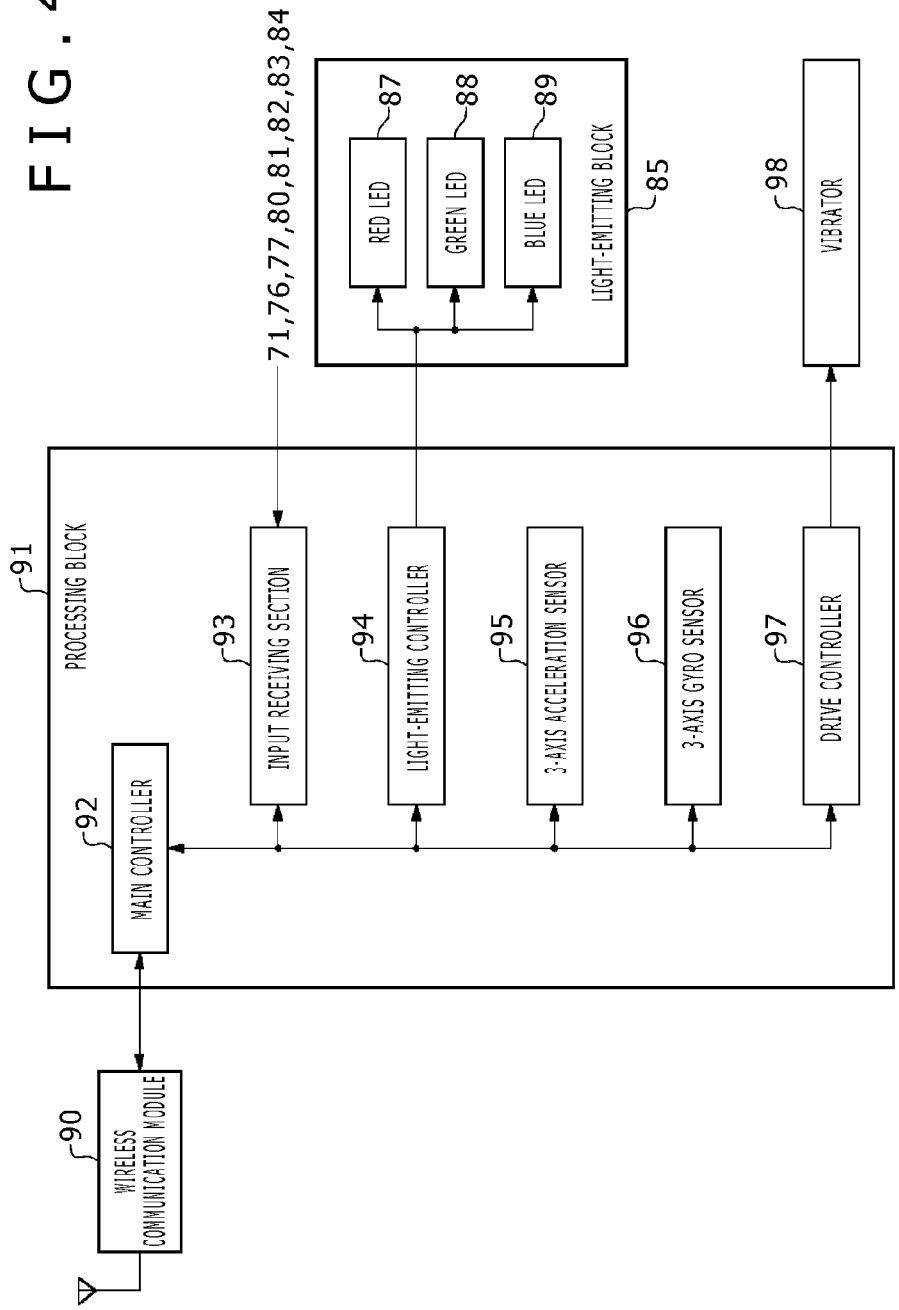
FIG. 4 is a diagram illustrating an internal configuration of the input apparatus.

Referring to FIG. 4, there is shown an internal configuration of the input device 6. The input device 6 has a wireless communication module 90, a processing block 91, a light-emitting block 85, and a vibrator 98. The wireless communication module 90 has a function of transmitting and receiving data with a wireless communication module of the information processing apparatus 10. The processing block 91 executes expected processing in the input device 6.

The processing block 91 has a main controller 92, an input receiving section 93, a light-emitting controller 94, a 3-axis acceleration sensor 95, a 3-axis gyro sensor 96, and a drive controller 97. The main controller 92 transmits and receives necessary data with the wireless communication module 90.

The input receiving section 93 receives input information from input blocks such as the direction key 71, the operation buttons 76, the analog sticks 77, and function button 80, the SHARE button 81, the OPTION button 82, the upper buttons 83, and the lower buttons 84, and transmits the received input information to the main controller 92. The main controller 92 converts the received input information into a predetermined control signal as required and supplies the resultant predetermined signal to the wireless communication module 90. The wireless communication module 90 transmits the received control signal to the information processing apparatus 10 with a predetermined timing. The light-emitting controller 94 controls the light emission of the red LED 87, the green LED 88, and the blue LED 89 that make up the light-emitting block 85.

In the information processing system 1 of the present embodiment, when the user presses the function button 80 with the input device 6 and the information processing apparatus 10 powered off, the input device 6 is powered on, the main controller 92 generates a connection request for connection with the information processing apparatus 10, and the wireless communication module 90 transmits the generated connection request to the information processing apparatus 10. The wireless communication module of the information processing apparatus 10 is in an active state even if the main power is off and, upon reception of the connection request, the information processing apparatus 10 turns on the main power to start up the OS (system software), thereby establishing wireless connection with the input device 6. The system software of the information processing apparatus 10 determines the turn-on light color of the light-emitting block 85 of the input device 6 that has transmitted the connection request and transmits the emitted light color information to the input device 6. At this moment, it is preferable that the system software analyzes the color information included in the space shot by the camera 7, identifies the color not included in the environmental colors as far as possible, and determines the emitted light color of the light-emitting block 85. Consequently, after turning on of the light-emitting block 85, the light-emitting block 85 turned on in the specified emitted light color can be preferably detected from the taken image captured by the camera 7.

The emitted light color information received by the wireless communication module 90 is passed to the main controller 92. The main controller 92 notifies the light-emitting controller 94 of the emitted light color information. This allows the light-emitting controller 94 to make the light-emitting block 85 emit light in the specified color.

The vibrator 98 is configured by an eccentric motor or the like and driven by the drive controller 97. The 3-axis acceleration sensor 95 detects an acceleration component in 3-axis direction (X, Y, and Z) of the input device 6, and the 3-axis gyro sensor 96 detects angular speeds in XZ plane, ZY plane, and YX plane.

Figure 5:
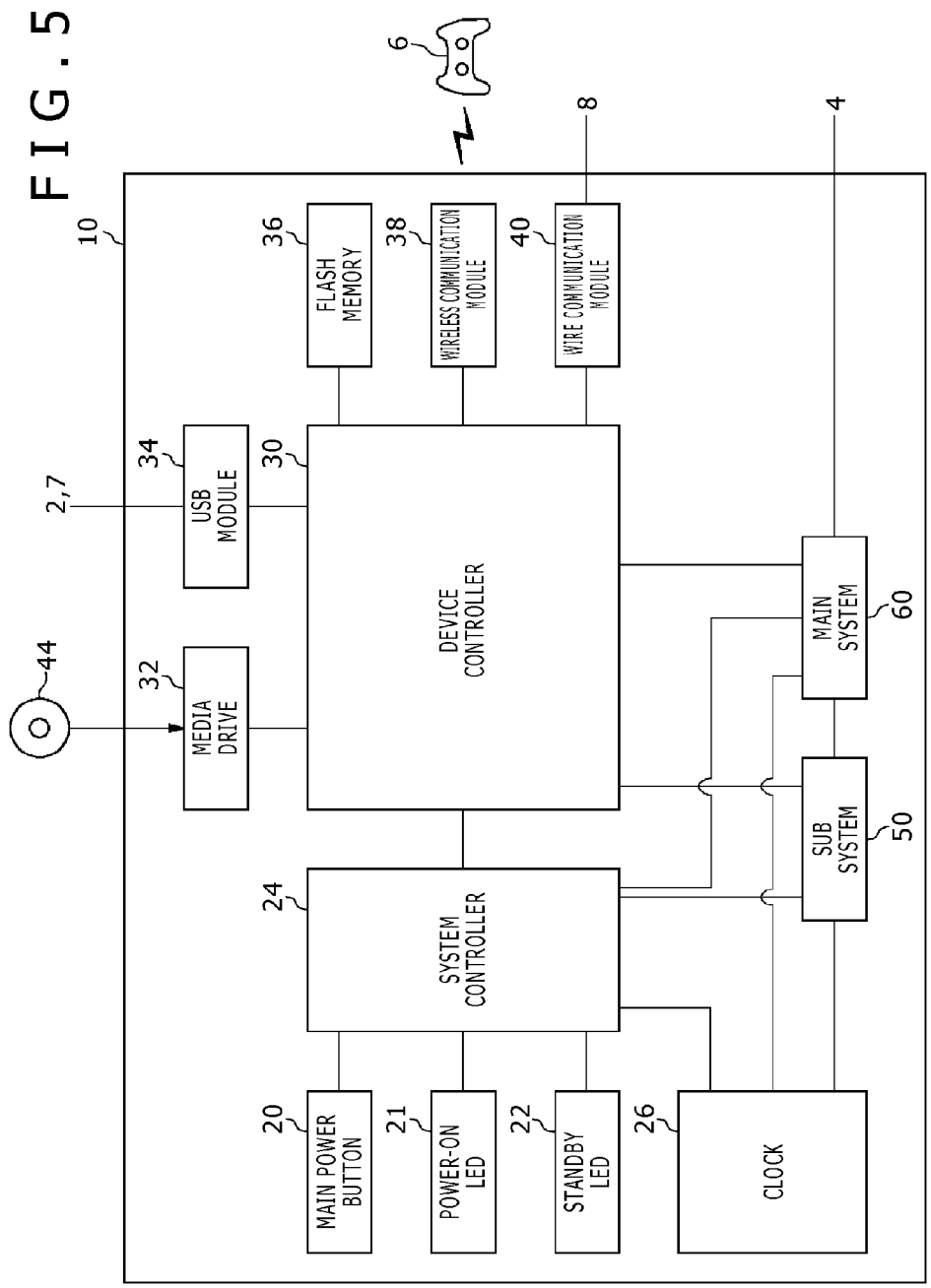
FIG. 5 is a diagram illustrating functional blocks of an information processing apparatus.

Referring to FIG. 5, there is shown a functional block diagram of the information processing apparatus 10. The information processing apparatus 10 is configured by a main power button 20, a power-on LED 21, a standby LED 22, a system controller 24, a clock 26, a device controller 30, a media drive 32, a USB module 34, a flash memory 36, a wireless communication module 38, a wired communication module 40, a sub system 50, and a main system 60.

The main system 60 is configured by a main CPU (Central Processing Unit) and the sub system 50 is configured by a sub CPU. The main CPU and the sub CPU operate exclusively with each other; namely, while the main CPU has been started up and is in an active state, the sub CPU is in a standby state and, while the sub CPU has been started up and is an active state, the main CPU is in a standby state. The main power button 20 is an input block on which the user executes operation input, arranged on the front surface of the housing of the information processing apparatus 10, and operated to turn on or off the power to the main system 60 of the information processing apparatus 10. That the main power is on denotes that the main system 60 is in an active state; that the main power is off denotes that the main system 60 is in a standby state. The power-on LED 21 is turned on when the main power button 20 is turned on and the standby LED 22 is turned on when the main power button 20 is turned off.

The system controller 24 detects the pressing of the main power button 20 by the user. When the main power button 20 is turned on with the main power being off, the system controller 24 gets this pressing operation as "on-instruction"; on the other hand, when the main power button 20 is pressed with the main power being on, the system controller 24 acquires this pressing operation as "off-instruction." It should be noted that, as described above, on/off of the main power can be controlled from the input device 6; when the function button 80 of the input device 6 is pressed with the main power being off, the system controller 24 acquires this button operation as "on-instruction."

Upon receiving an on-instruction, the system controller 24 notifies the sub system 50 in an active state of a detection result and, at the same time, turns off the standby LED 22 and turns on the power-on LED 21. At this moment, the sub system 50 starts up the main system 60, thereby getting into a standby mode. On the other hand, upon receiving an off instruction, the system controller 24 notifies the main system 60 in an active state of a detection result and, at the same time, turns off the power-on LED 21 and turns on the standby LED 22. At this moment, the main system 60 starts up the sub system 50, thereby getting into a standby mode. The clock 26 is a realtime clock to generate current date and time information and supplies the generated current date and time information to the system controller 24, the sub system 50, and the main system 60.

The device controller 30 is configured as an LSI (Large-Scale Integrated Circuit) that executes the transfer of information between devices like a south bridge. As shown, the device controller 30 is connected to devices such as the system controller 24, the media drive 32, the USB module 34, the flash memory 36, the wireless communication module 38, the wired communication module 40, the sub system 50, and the main system 60. The device controller 30 absorbs differences in electric characteristics and data transfer speeds between devices, thereby controlling data transfer timing.

The media drive 32 is a drive unit that drives a loaded ROM media 44 recorded with application software such as games and reads programs and data from the ROM media 44. The ROM media 44 is a read-only recording media such as an optical disc and a Blu-ray disc.

The USB module 34 is a module that is connected to external devices with USB cables. The USB module 34 may be connected to the auxiliary storage apparatus 2 that is a hard disk drive with a USB cable. In addition, the USB module 34 may be connected to the camera 7 with a USB cable. The flash memory 36 is an auxiliary storage apparatus that provides an internal storage. The wireless communication module 38 communicates with the input device 6 for example in a wireless manner by a communication protocol such as Bluetooth (trademark) protocol or IEEE802.11 protocol. It should be noted that the wireless communication module 38 may be compliant with the third-generation (3rd Generation) digital mobile phone system based on the IMT-2000 (International Mobile Telecommunication 2000) specified by ITU (International Telecommunication Union). The wired communication module 40 communicates with external devices in a wired manner and is connected to the network 3 via AP8 for example.

The main system 60 has the main CPU, a memory that is a main storage apparatus and a memory controller, and GPU (Graphics Processing Unit). These functions may be configured as a system-on-chip and formed on one chip. The main CPU has a function of starting up the OS and executing applications installed in the auxiliary storage apparatus 2 under an environment provided by the OS.

Figure 6:
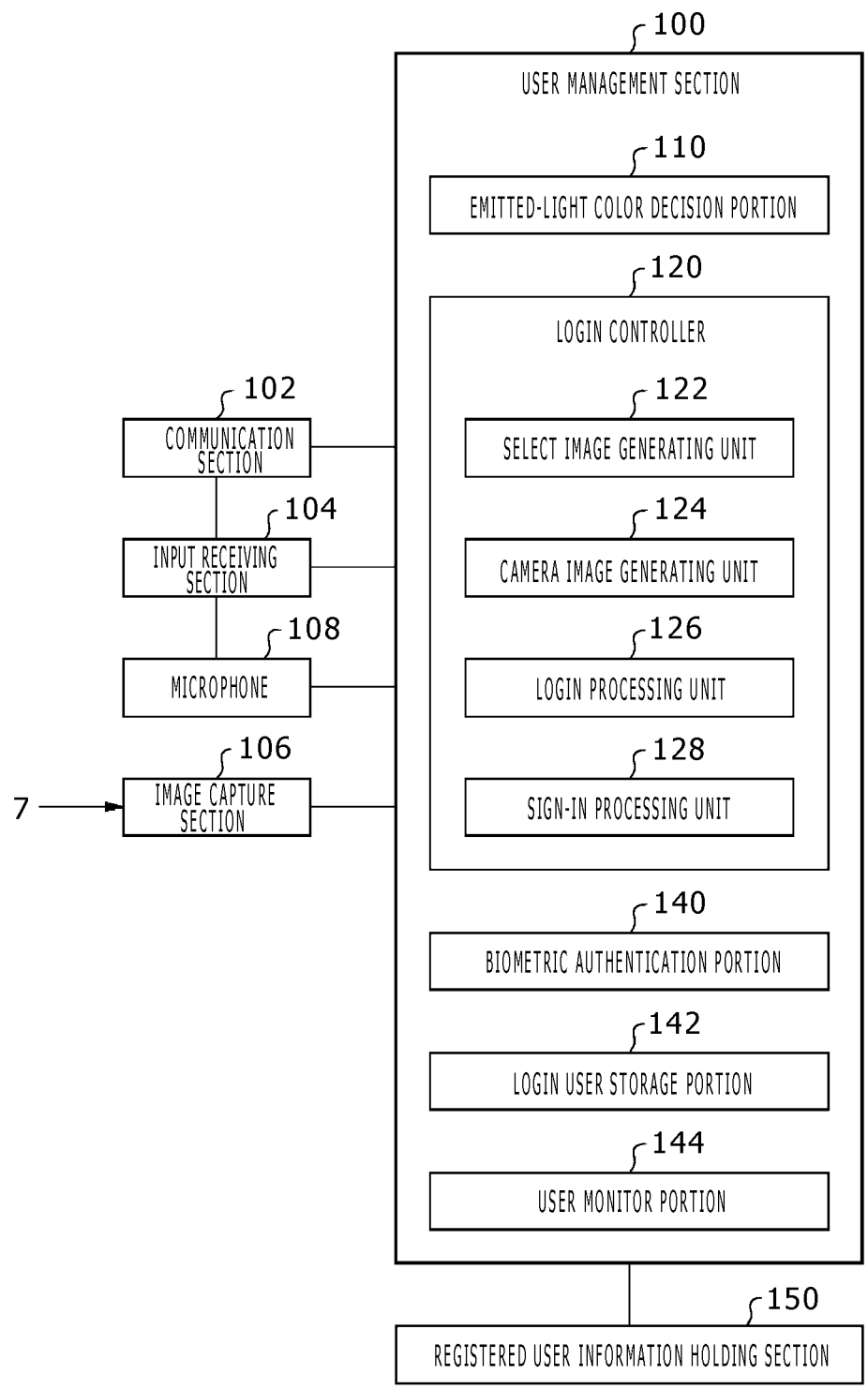
FIG. 6 is a diagram illustrating an internal configuration of the information processing apparatus.

Referring to FIG. 6, there is shown an internal configuration of the information processing apparatus 10. The information processing apparatus 10 has a communication section 102, an input receiving section 104, an image capture section 106, a microphone 108, a user management section 100, and a registered user information holding section 150. The user management section 100 is realized by the OS (system software) of the information processing apparatus 10 and an application that is executed by the OS and has an emitted-light color decision portion 110, a login controller 120, a biometric authentication portion 140, a login user storage portion 142, and a user monitor portion 144. The communication section 102 is indicative of functions of the wireless communication module 38 and the wired communication module 40 shown in FIG. 5.

In FIG. 6, the elements described as function blocks that execute various types of processing can be configured by a circuit blocks, memories, and other LSIs in terms of hardware; in terms of software, these functional blocks are realized by programs and so on loaded in memories. Therefore, it is known by those skilled in the art that these functional blocks can be realized by only hardware, only software, or combinations thereof without limitation to any thereof.

One of the features of the OS of the information processing apparatus 10 according to the present embodiment is to support simple login operations by two or more users. In order to log in on the OS of the information processing apparatus 10, each user must acquire a user account. In what follows, a user account necessary for logging in on the information processing apparatus 10 is referred to as a "local account." When a user uses the information processing apparatus 10 for the first time, the user registers the local account into the information processing apparatus 10 by following a predetermined procedure. At this time, registering a combination of keys of the input device 6 as a pass code in advance, the user can prevent a situation where another user executes login with the local account of the user concerned. In addition, in the information processing apparatus 10, when the user registers the local account, the user also registers his or her face photograph and/or data indicative of the feature quantity of the face image for face identification in advance. This face image or the feature quantity data is used for realizing a simple login operation.

It should be noted that the server 5 holds the accounts (hereafter referred to as "network accounts") of users who use the information processing system 1. Each network account is linked to a user and is related with the online ID (a nickname on a network) for example of the user. If the user used information processing apparatuses (game devices) of old generations in the past, it is often that the user already has a network account in the information processing system 1. In registering a local account, the information processing apparatus 10 relates this local account with the network account. This allows the user to store trophies won by using the information processing apparatus 10 and game save data into the server 5.

It should also be noted that, if the user does not have a network account, the user signs in on the server 5 by use of the information processing apparatus 10, to be more specific, registers the sign-in ID (email address) and the password, thereby getting the network account from the server 5.

The initial registration of a local account described above allows the user's local account, key combination information (pass cord), network account, sign-in ID, password, online ID, and face image and/or face image feature quantity data to be stored in the registered user information holding section 150 as registered user information. In what following, a face image and face image feature quantity data may be generically referred to as a face image. It should be noted that, in the information processing apparatus 10, a user icon representative of each user may be stored in the registered user information holding section 150 as one of the registered user information. Here, the local account is used to log in on the OS of the information processing apparatus 10 and the network account is used for the user to sign in on the server 5. When the local account is set to the registered user information holding section 150, then, the user need not execute this registration operation. In the information processing apparatus 10, a least user A, user B, and user C have registered the user information including the local accounts and the face images; therefore, these users can log in on the information processing apparatus 10. It is assumed here that the online ID of user A be "TARO," the online ID of user B be "HANAKO," and the online ID of user C be "JIRO."

<Login Processing 1>

The following describes an example of the processing that is executed when a registered user logs in on the OS of the information processing apparatus 10. In this login processing 1, the user executes login by use of the input device 6.

When the user presses the function button 80 of the input device 6, this pressing information is transmitted to the information processing apparatus 10. In the information processing apparatus 10, the communication section 102 receives the pressing information as a connection request to connect the input device 6 to the communication section 102. It should be noted that, if the main power to the information processing apparatus 10 is off, then the communication section 102 is connected to the input device 6 after the main power to the information processing apparatus 10 is turned on by the pressing information of the function button 80. At the same time, the pressing information of the function button 80 is transmitted to the input receiving section 104. The input receiving section 104 receives this pressing information as a login request from the user, transmitting this received pressing information to the user management section 100.

When the login request is received by the input receiving section 104, each of the functions in the user management section 100 is realized. The user management section 100 may be realized by the execution of the user management application.

The emitted-light color decision portion 110 decides an emitted light color of the light-emitting block 85 of the input device 6 that transmitted a login request. The image capture section 106 captures a taken image from the camera 7. For example, the camera 7 takes images of the space periodically (every 1/30 second for example) and provides the taken images to the image capture section 106 via the USB module 34. It is preferable for the emitted-light color decision portion 110 to identify colors that does not exist in the taken space from the taken image and decide an emitted light color from the identified colors. When the emitted-light color decision portion 110 has decided an emitted light color, the communication section 102 transmits the emitted light color information to the input device 6. In the input device 6, the wireless communication module 90 receives the emitted light color information and the light-emitting controller 94 turns on the light-emitting block 85 in the emitted light color according to the emitted light color information. For example, if the emitted light color information specifies red, the light-emitting block 85 of the input device 6 is turned on in red.

The biometric authentication section 140 compares the user's biometric information included in a taken image with the biometric information held in the registered user information holding section 150 and determines whether the shot user is one of the users registered in the information processing apparatus 10. To be more specific, the biometric authentication section 140 compares the face image of user included in a taken image with the face images held in the registered user information holding section 150 and, if the taken face image is found among the registered face images, determines that the taken user is a registered user, thereby identifying the taken user. It should be noted that the biometric authentication section 140 compares the feature quantity of the face image of user included in the taken image with the feature quantity data of the face images held in the registered user information holding section 150 and, if the feature quantity data of the taken face image is found matching among the feature quantity data of registered face images, then determines that the taken user is a registered user, thereby identifying the taken user. In the present embodiment, it is assumed that the biometric authentication section 140 be a face recognition system; however, it is also practicable for the biometric authentication section 140 to be a biometric authentication system that compares, by use of an imaging apparatus, other biometric information such as finger print, hand geometry, retina, iris, and blood vessel, for example, with the biometric information registered in advance. The following describes an example in which the biometric authentication section 140 determines that a taken face image matches the face image of a registered user.

The login controller 120 determines that the login of the user has been rejected. In the information processing apparatus 10 of the present embodiment, in determining the rejection of user login by the login controller 120, a user interface is provided to facilitate user login on the basis of an authentication result obtained by the biometric authentication portion 140.

To be specific, the select image generating unit 122 reads registered user information held in the registered user information holding section 150 and generates a select screen for selecting users registered in the information processing apparatus 10. To be more specific, of the registered user information, the select image generating unit 122 reads user icons and online IDs and generates a select screen on which the online IDs of registered users are arranged in a list. This select screen makes up a login screen in login processing 1.

Referring to FIG. 7(a), there is shown one example of a select screen. The select image generating unit 122 reads the user icons and the online IDs of all registered users held in the registered user information holding section 150 and displays the read user icons and online IDs in a list that is readable by the user. In what follows, user icon and online ID are referred to as "user identification information." In the select screen, the login processing unit 126 displays a focus frame 200 enclosing one piece of user identification information in a movable manner on the list. The user operates the input block of the input device 6 to move the focus frame 200 to the display area of own user identification information and presses the enter key (the X button 73) of the input device 6 to select the own user identification information. Here, let the user requesting login be user A and, when the user selects "TARO" on the select screen by operating the input device 6a, then the login processing unit 126 generates an input screen of key combinations shown in FIG. 7(b). Here, when user A enters a registered key combination, the login processing unit 126 determines whether the entered key combination is the same as the key combination of user A held in the registered user information holding section 150, thereby determining whether the login by user A is permitted or not. In this sequence of login tasks, the login processing unit 126 receives only the operation information from the input device 6a and therefore does not receive any operation information from the input device 6 other than the input device 6a.

In the select screen shown in FIG. 7(a), the login processing unit 126 arranges the focus frame 200 in a display area of the user identification information of the user face-recognized by the biometric authentication portion 140. Consequently, user A is provided with the select screen with the focus frame 200 arranged in the display area of own user identification information, so that user A need not move the focus frame 200 by operating the input device 6a, allowing user A to log in only by pressing the enter key, thereby realizing user's simple login tasks.

It should be noted that, if a user imaged by the biometric authentication portion 140 is found to be a registered user, the login processing unit 126 allows this user to log in without presenting a select screen generated by the select image generating unit 122. If this depends on the accuracy of the biometric authentication by the biometric authentication portion 140 and realizes precision biometric authentication, it is practicable for a user to log in by the login processing unit 126 only on a decision result obtained by the biometric authentication portion 140. For example, if the biometric authentication portion 140 executes finger print authentication, which is high in the reliability in authentication results, a user may log in without presenting a select screen. It should be noted that, if the select operation in a select screen is skipped, the pass code shown in FIG. 7(b) must be entered. Further, for a user whose pass code is not registered in the registered user information holding section 150, the select operation in a select screen may be made essential.

In addition, in a select screen, the number of display pieces of user identification information is limited, a maximum of four in the example shown in FIG. 7(a). If the number of registered users is higher than four, then the user can scroll the list of user identification information to the left or to the right by operating the input block of the input device 6. The select image generating unit 122 may arrange the user identification information in the order in which the date and time of user's last login (or last logoff) is closer to the present time. In the example shown in FIG. 7(a), "TARO" is arranged the first (standard position) followed by "HANAKO," "JIRO," and "SABURO" in this order to the right side, which denotes that the last login date is closer to the current date and time in the order of "TARO," "HANAKO," "JIRO," and "SABURO."

It should be noted that the select image generating unit 122 may arrange user identification information in accordance with authentication results obtained by the biometric authentication portion 140. The biometric authentication portion 140 derives the degree of coincidence between a taken face image of user and the face images of all users held in the registered user information holding section 150. As described above, the biometric authentication portion 140 may derive the degree of coincidence by the comparison of the feature quantity data of face images. This degree of coincidence is expressed by numerals and the degree of coincidence is derived in the form of points out of 100 points for example. If the degree of coincidence of a registered face image is 90 points or higher, then the biometric authentication portion 140 determines that the taken user is the user of that face image, transmitting this result to the login controller 120; if the face images of two brothers of the same sex are registered for example, it is possible that, because of the similarity between these two face image is considered to be high, the degree of coincidence of each of these face images is 90 points or higher. Therefore, the select image generating unit 122 may receive the degrees of coincidence of two or more registered face images from the biometric authentication portion 140 and arrange the user identification information in the order of higher degrees of coincidence starting from the standard position. Consequently, if the user identification information with the focus frame 200 arranged by the login processing unit 126 is not of the own user identification information, own user identification information is arranged in the neighborhood thereof, so that a task of finding own user identification information in the select screen can be skipped.

Figure 8:
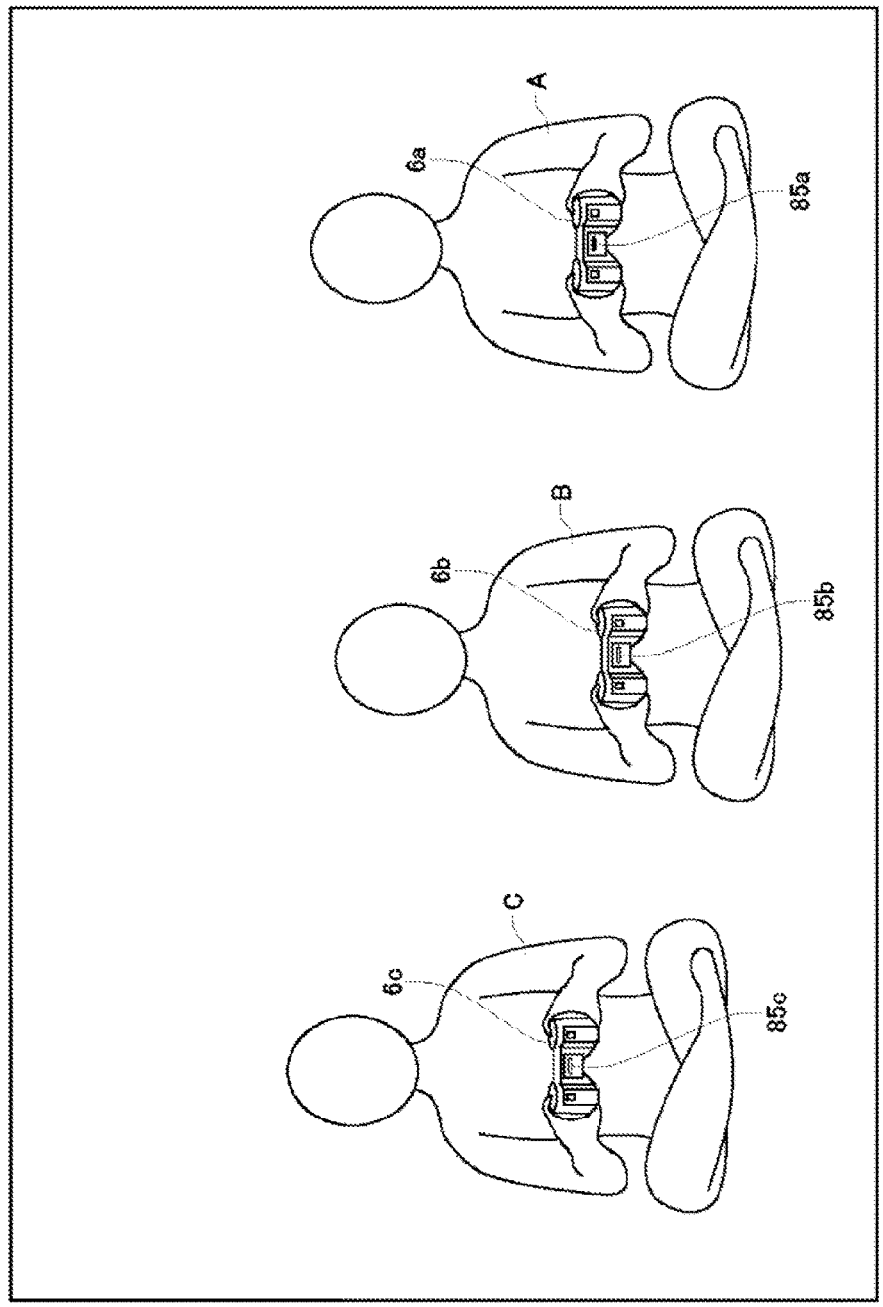
FIG. 8 is a diagram illustrating one example of images taken by a camera.

The following describes a specific login processing procedure. Referring to FIG. 8, there is shown one example of an image taken by the camera 7. The biometric authentication portion 140 extracts human faces from the taken image and compares the extracted face images with the face images registered in the registered user information holding section 150, thereby executing the identification of humans included in the taken image. In this example, users A, B, and C who are registered users are included in the taken image, so that the biometric authentication portion 140 identifies that the three humans in the taken image are user A, B, and C from the right side.

The login processing unit 126 executes the above-mentioned user login support processing in the order in which the function button 80 of the input device 6 was pressed. In the present embodiment, assume that the function button 80 of each of the input device 6a, the input device 6b, and the input device 6c be pressed in the order of users A, B, and C. Then, the emitted-light color decision portion 110 generates emitted light information of red to the input device 6a, emitted light information of green to the input device 6b, and emitted light information of blue to the input device 6c and the communication section 102 transmits these emitted light information to these input devices 6. Receiving the emitted light information, each input device 6 turns on the light-emitting block 85 in the color specified by the received emitted light information. Therefore, the light-emitting block 85a of the input device 6a is turned in red, the light-emitting block 85b of the input device 6b is turned in green, and the light-emitting block 85c of the input device 6c is turned in blue. The emitted light information of each input device 6 is transmitted to the login controller 120 from the emitted-light color decision portion 110, upon which the login processing unit 126 recognizes the turn-on color of each input device 6 that is identifiable by the game controller ID.

The login processing unit 126 executes login support processing in the order of users A, B, and C. The login processing unit 126 recognizes that the light-emitting block 85a of the input device 6a is turned on in red and searches the taken image for a long rectangular red area for example. Upon detecting the red area in the taken image, the login processing unit 126 understands from an authentication result obtained by the biometric authentication portion 140 that a face image existing in the neighborhood of this red area is user A. It should be noted that the input device 6a and the user may be related with each other by the identification of a face image existing in the upper portion of the red area in the taken image. Consequently, it is understood that user A is using the input device 6a that turned on the light-emitting block 85a in red. For example, the biometric authentication portion 140 provides, as an authentication result, a camera coordinate value in which the face image of each user is imaged to the login controller 120 along with the information for identifying each user and the login processing unit 126 compares the camera coordinate value of the detected red area with the camera coordinate value of the face image, thereby recognizing that the user having the input device 6a turned red is user A. The login processing unit 126 arranges the focus frame 200 on the user identification information of user A in the select screen and, when user A presses the enter key of the input device 6a, determines whether a key combination that is entered on the input screen shown in FIG. 7(b) is that of user A, thereby determining whether user A can log in or not. If the entered key combination is found to be that of user A, then, the login processing unit 126 permits the login of user A. Then, the login processing unit 126 stores, in the login user storage portion 142, login information, namely the information (the user account) for identifying user A, the information (the game controller ID) for identifying the input device 6a that is used by user A, and the information (the red emitted light information) for identifying the input device 6a included in the taken image, by relating these items of information with each other. It should be noted that the information for identifying the input device 6a included in the taken image denotes the information that can identify the input device 6a by image analyzing the taken image by the login processing unit 126.

When the login of user A has been completed, the login processing unit 126 executes the login support processing of user B who uses the input device 6b. The login processing unit 126 recognizes that the light-emitting block 85b of the input device 6a is turned on in green and searches the taken image for a long rectangular green area for example. Upon detecting the green area in the taken image, the login processing unit 126 understands from an authentication result obtained by the biometric authentication portion 140 that a face image existing in the neighborhood of this green area is user B. Consequently, it is understood that user B is using the input device 6*b* that turned on the light-emitting block 85*b* in green. The login processing unit 126 arranges the focus frame 200 on the user identification information of user B in the select screen and, when user B presses the enter key of the input device 6*b*, determines that a key combination that is entered on the input screen shown in FIG. 7(*b*) is that of user B, thereby identifying the account of user B to permit login. Subsequently, the login processing unit 126 executes the login support processing of user C who uses the input device 6*c*. The login processing unit 126 stores, in the login user storage portion 142, the login information, namely the logged in user account, the information for identifying the input device 6 to be used by the user, and the emitted light information of the input device 6 by relating these items of information with each other.

As described above, in the permission of login, the login processing unit 126 relates each user with the input device 6 used by that user, so that the OS can identify the user of each input device 6. The OS transmits the information about the relationship of users and the input devices 6 to a game or the like, so that the game can understand that an operation signal from the input device 6*a* is by user A for example, thereby being capable of the user management of save data and granted trophies. In addition, the login processing unit 126 stores also the emitted light information of the input device 6 into the login user storage portion 142 as one of login information, so that the user monitor portion 144 to be described later can determine from a taken image whether the user is using own input device 6.

When the login processing unit 126 permits the login of a user, the sign-in processing unit 128 has the user automatically sign in on a network service provided by the server 5. This automatic sign-in is executed by use of the user information (the network account) registered in the registered user information holding section 150. When the user logs in on the information processing apparatus 10, the automatic sign-in on a network service allows the skipping of the manual sign-in tasks by the user.

It should be noted that, in generating a select image, the select image generating unit 122 preferably does not include the user identification information of any already logged-in users in the select image. This prevents a user to be logged in from mistakenly selecting the online ID of an already logged-in user.

As described above, the login processing for two or more users is completed. It should be noted that, in the above-mentioned example, users A, B, and C log in at the same time; it is also practicable for a new user to log in halfway after starting a game by pressing the function button 80 of the input device 6.

As described above, the login user storage portion 142 stores login users and the emitted light information of the input device 6 as login information by relating these items of information with each other, so that the user monitor portion 144 can monitor the relation between the information (the emitted light information) for identifying the input device 6 included in a taken image and the user account, and detect that the user selected a wrong input device 6 from the image taken by the camera 7. The following assumes that two or more users A, B, and C play a game together after the login.

During a game play, each user holds the input device 6, so that the possibility for each user to basically has a wrong input device 6 is low. If the case where the users suspend a game play and resume after a rest, each user remembers the emitted light color of the light-emitting block 85 of the input device 6 and takes up the input device 6 by recognizing that the input device 6*a* of which light-emitting block 85 is emitting red in the case of user A for example. However, there is still possibility that a user takes up a wrong input device 6.

Hence, in the user management section 100, the user monitor portion 144 monitors whether each user is using own input device 6 on the basis of the relation between the user stored in the login user storage portion 142 and the input device 6. Here, the relation stored in the user monitor portion 144 denotes the relation that user A uses the input device 6*a* turned on red, user B uses the input device 6*b* turned on green, and user C uses the input device 6*c* turned on blue. The biometric authentication portion 140 extracts the face image of each user included in the image taken by camera 7 and compares the extracted face image with the face image of each registered user stored in the registered user information holding section 150, thereby identifying each user included in the taken image. The user monitor portion 144 searches the taken image for a long rectangular red area, green area, and blue area, and determines whether the face image existing in the neighborhood of the red area is that of user A, the face image existing in the neighborhood of the green area is that of user B, and the face image existing in the neighborhood of the blue area is that of user C. If the result of this decision is OK, namely, if the relation between the user and the input device 6 is right, then the user monitor portion 144 recognizes that each user is properly using own input device 6. On the other hand, if the result of this decision is NG, namely, the relation between the user and the input device 6 is wrong, then the user monitor portion 144 generates a warning message indicative of the wrong decision result and transmits this message from the output device 4.

If user B holds the input device 6*c* turned on blue and user C holds the input device 6*b* turned on green, for example, then the user monitor portion 144 generates a warning message indicative that user B and user C hold wrong input devices 6 and displays the generated warning message on the output device 4. Receiving this notification, users B and C can recognize that users B and C have wrong input devices 6. When users B and C exchanges the input devices 6 to have rightful input devices 6, then the user monitor portion 144 may generate a message indicative that users B and C have the rightful input devices 6 to display the generated message on the output device 4.

The user monitor portion 144 may monitor the relation between the user and the input devices 6 on a periodical basis. This allows the instant detection of wrong input devices 6 if any and notify the users thereof. On the other hand, as described above, it is considered that, during a game play, users are always holding input devices 6, there are few chances of users' having wrong input devices 6. Therefore, the user monitor portion 144 may determine, on the basis of a sensor detected value information transmitted from the input device 6, whether or not the input device 6 is being used (namely, the input device 6 is being held or not), and do not do monitor processing during the use of the input device 6. Consequently, the CPU load in the information processing apparatus 10 can be lowered. The user monitor portion 144 may do monitor processing when the sensor detected value information transmitted from the input device 6 is indicative that the input device 6 is in an unused state and then subsequent sensor detected value information of the input device 6 is indicative that the input device 6 has been moved.

<Login Processing 2>

The following describes another example in which a registered user logs in on the OS of the information processing apparatus 10. In this login processing 2, the user executes login without use of the input device 6.

When the user presses the main power button 20 of the information processing apparatus 10, the main power to the information processing apparatus 10 is turned on, upon which the input receiving section 104 receives main power pressing information as a login request from the user. When the input receiving section 104 receives the login request, each of the functions of the user management section 100 is realized. The user management section 100 may be realized by the execution of a user management application.

It should be noted that, if the main power to the information processing apparatus 10 is already on, the utterance of a login word by the user executes the user management application. In the information processing apparatus 10, the user utterance is picked up by the microphone 108 and, if this utterance is a predetermined login word, "I'll log in" for example, then the input receiving section 104 receives the voice information as a login request from the user. When the login request is received by the input receiving section 104, each of functions of the user management section 100 is realized.

The biometric authentication portion 140 compares the biometric information of a user included in the taken image with the biometric information held in the registered user information holding section 150 to determine whether the imaged user is a user registered in the information processing apparatus 10 or not. To be more specific, the biometric authentication portion 140 compares the face image of a user included in the taken image with a face image held in the registered user information holding section 150 to determine that the imaged user is a registered user if a taken face image is found in the registered face images. In what follows, an example is described in which the biometric authentication portion 140 determines that a taken face image is found matching the face image of a registered user.

Figure 9:
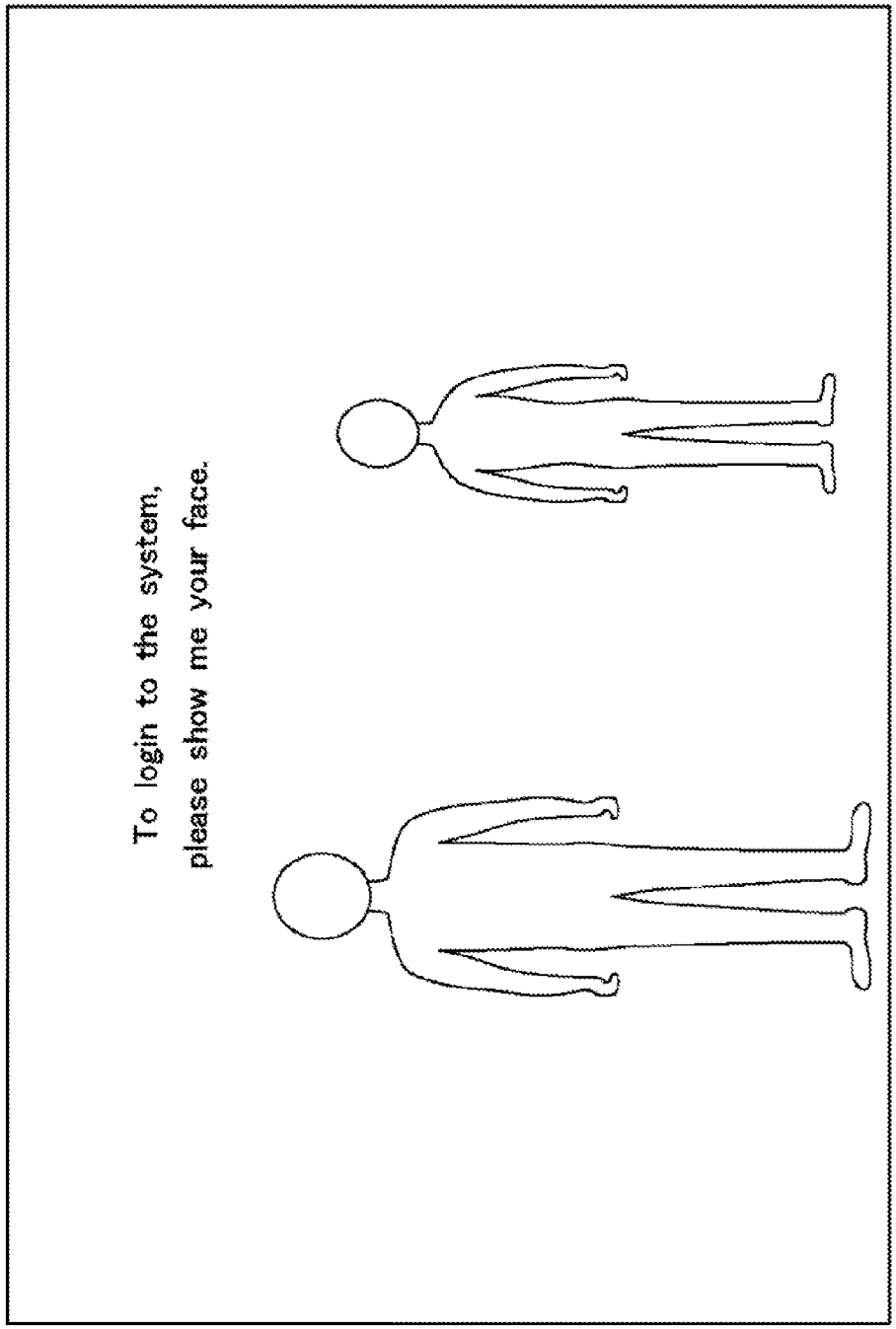
FIG. 9 is a diagram illustrating a camera image displayed on an output apparatus.

The login controller 120 determines the rejection of user login. In the information processing apparatus 10 of the present embodiment, when the login controller 120 determines the rejection of user login, a user interface for facilitating user login is provided on the basis of an authentication result obtained by the biometric authentication portion 140. In login processing 2, the camera image generating unit 124 outputs the taken image captured by the image capture section 106 to the output device 4 as a login screen. Consequently, the video taken by the camera 7 is displayed on the output device 4. Referring to FIG. 9, there is shown a camera image displayed on the output device 4. Here, two users are imaged.

Figure 10:
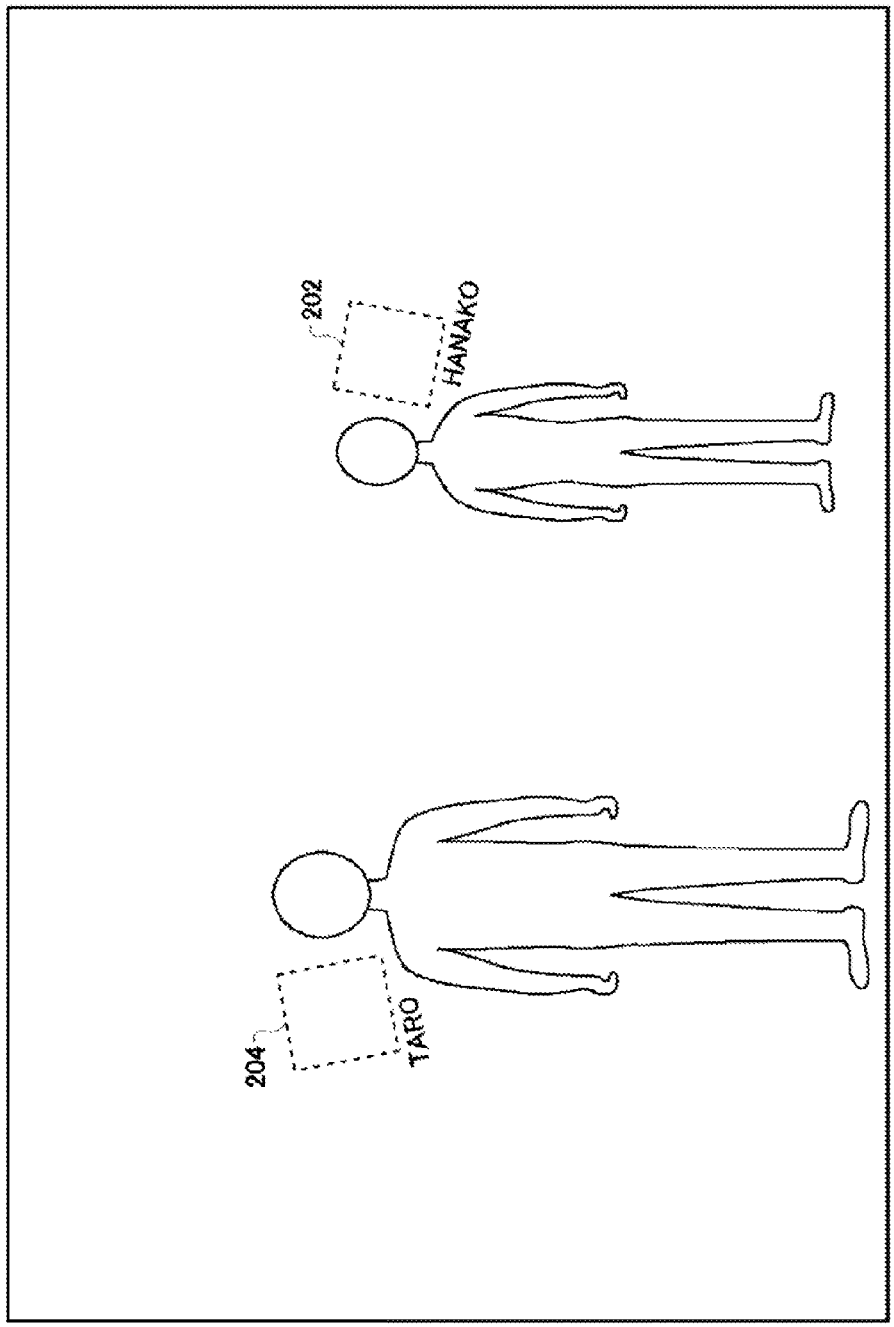
FIG. 10 is a diagram illustrating one example of a login screen.

Referring to FIG. 10, there is shown one example of a login screen. The biometric authentication portion 140 recognizes and identifies each user by the face authentication processing of each user. When the face recognition processing has been completed, the login processing unit 126 displays face frames 202 and 204 on around the faces of users. At this moment, the login processing unit 126 displays the online IDs of users authenticated by the biometric authentication portion 140 in the neighborhood of the face frames 202 and 204. Each user check the online IDs and, if an online ID is own online ID, then the user moves own face into the face frame 202 or 204. This face operation corresponds to a decision operation for login and, upon detection of the movement of the face by the user to the face frame 202 or 204, the login processing unit 126 logs this user in.

Assuming that the user move only the face at the same position, the login processing unit 126 displays the face frame 202 or 204 with a slight inclination in the neighborhood of the face. Consequently, the user need not move the legs and can easily put the face into the face frame 202 or 204. It should be noted that the login processing unit 126 displays the face frames 202 and 204 at positions that do not overlap with the faces of the users.

In login processing 2, an operation of moving faces to the face frames 202 and 204 is one example of a decision operation for login and corresponds to the pressing of the enter key on the select screen in login processing 1; it is also practicable to allocate another operation to the login decision operation. For example, if the face frames 202 and 204 are displayed around the face images in the taken image and the user nods in this state, this operation may be processed as a login decision operation. Also, a predetermined operation such as shaking a hand may be allocated to a login decision operation.

Detecting the movement of the face into the face frame 202 or 204, the login processing unit 126 generates an input screen of a key combination shown in FIG. 7(b). It should be noted that a pass code input screen may be presented every time the face of each user is detected to have been moved to the face frame or sequentially presented to each user after the detection of the movement of the faces of all registered users to the face frames.

Figure 11:
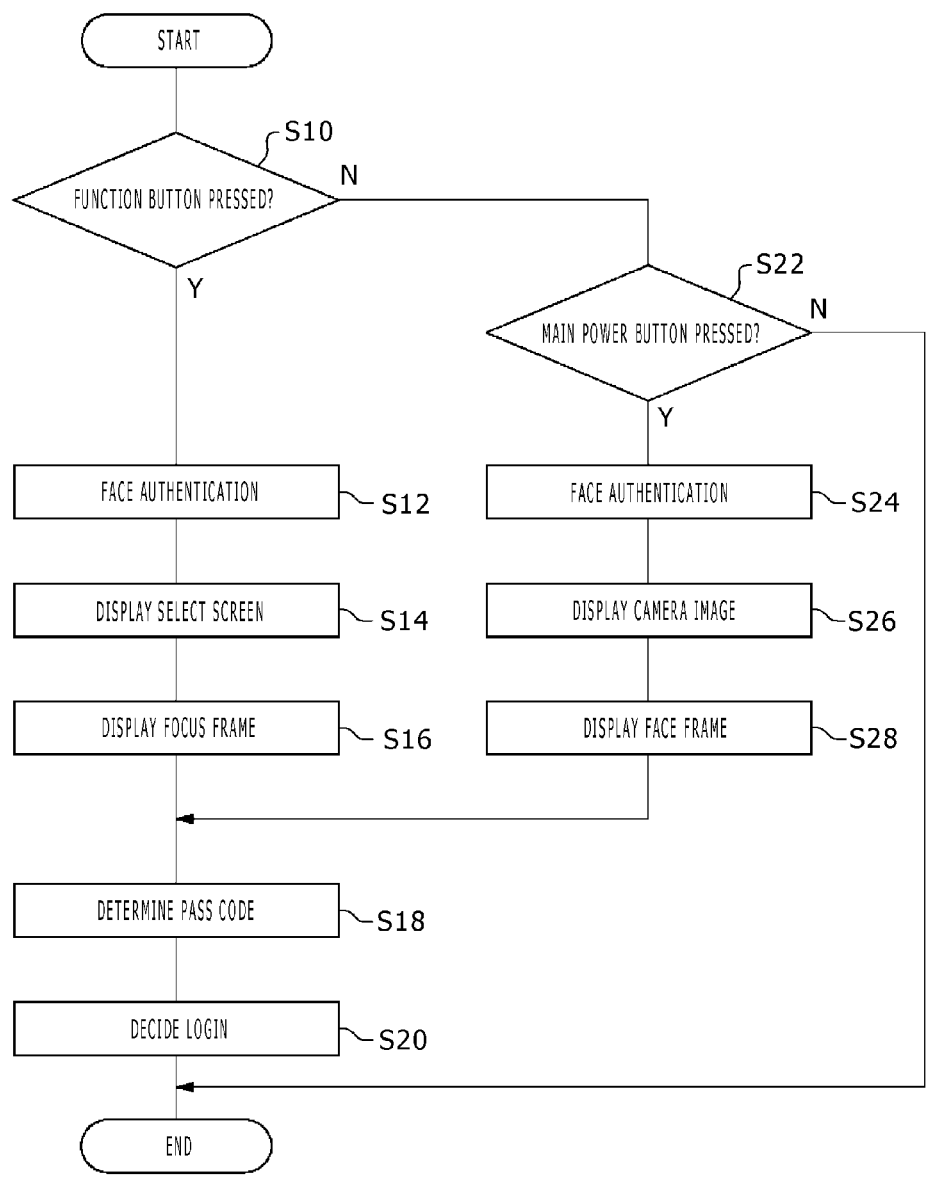
FIG. 11 is a flowchart indicative of login processing in the information processing apparatus.

Referring to FIG. 11, there is shown a flowchart indicative of login processing that is executed in the information processing apparatus 10. The information processing apparatus 10 realizes two login processing operations which are selectively executed in accordance with types of login requests from a user.

In the information processing apparatus 10, the input receiving section 104 receives two types of login requests. The first login request is generated by pressing the function button 80 of the input device 6 by the user. The second login request is generated when the main power button 20 of the information processing apparatus 10 is pressed by the user or the microphone 108 picks up the utterance of a predetermined login word by the user.

If the input receiving section 104 receives a login request generated by pressing the function button 80 (Y in S10), then the biometric authentication portion 140 determines whether the face image included in a taken image of the camera 7 is one of two or more face images held in the registered user information holding section 150 and, if the decision is yes, that registered user is identified (S12). The select image generating unit 122 generates a select image in which information (user identification information) for identifying two or more registered users held in the registered user information holding section 150 is arranged in an appropriate manner and displays the generated select image on the output device 4 as a login screen (S14). In this select image, in order for the user to be able to select own user identification information only by pressing the enter key of the input device 6, the login processing unit 126 brings the focus frame 200 to the user identification information of the user found to be a registered user (S16). When the user presses the enter key, the login processing unit 126 generates a pass code input screen and, if the pass code entered by the user is found matching (S18), then makes this user log in on the system (S20).

If the input receiving section 104 receives a login request generated when the main power button 20 is turned on or a login request via the microphone 108 (Y in S22) rather than a login request generated when the function button 80 is pressed (N in S10), the biometric authentication portion 140 determines whether the face image included in a taken image of the camera 7 is one of the two or more face images held in the registered user information holding section 150 and, if the decision is yes, identifies that registered user (S24). The camera image generating unit 124 displays the taken image of the camera 7 on the output device 4 as a login screen (S26). The login processing unit 126 displays the predetermined face frame 202 in the neighborhood of the face image of the user included in the taken image (S28) and, when the user moves the face into the face frame 202, receives this operation as a login decision operation. Subsequently, the login processing unit 126 generates a pass code input screen and, if the pass code entered by the user is found matching (S18), makes that user log in on the system (S20). It should be noted that, if the operation of pressing the main power button 20 has not also executed (N in S22), then the login processing is not executed.

As described above, the information processing apparatus 10 executes two types of login processing. One of the features of login processing 1 that is executed by pressing the function button 80 is to relate the user with the input device 6; another feature is not to present a taken image of the camera 7 to the user. Namely, the information processing apparatus 10 executes the face authentication processing using a taken image without making users aware of the face authentication processing. On the other hand, in login processing 2 that is executed by pressing the main power button 20, a taken image of the camera 7 is explicitly presented to the user as a login screen. Namely, that the face authentication processing is being executed is implicitly indicated to the user, in which the select screen shown in FIG. 7(a) is not present to the user. Thus, in accordance with the types of login processing, the information processing apparatus 10 provides different user interfaces that are intuitively understandable to the user, thereby supporting user's simple login operations.

While the present invention has been described on the basis of an embodiment thereof, it is to be understood by those skilled in the art that this embodiment is illustrative only and therefore changes and variations may be made to combinations of each component of the embodiment and each processing process without departing from the scope of the present invention.

REFERENCE SIGNS LIST

1 . . . Information processing system, 4 . . . Output device, 6 . . . Input device, 7 . . . Camera, 10 . . . Information processing apparatus, 20 . . . Main power button, 38 . . . Wireless communication module, 40 . . . Wired communication module, 50 . . . Sub system, 60 . . . Main system, 80 . . . Function button, 85 . . . Light-emitting block, 87 . . . Red LED, 88 . . . Green LED, 89 . . . Blue LED, 90 . . . Wireless communication module, 91 . . . Processing block, 92 . . . Main controller, 93 . . . Input receiving section, 94 . . . Light-emitting controller, 95 . . . 3-axis acceleration sensor, 96 . . . 3-axis gyro sensor, 97 . . . Drive controller, 98 . . . Vibrator, 100 . . . User management section, 102 . . . Communication section, 104 . . . Input receiving section, 106 . . . Image capture section, 108 . . . Microphone, 110 . . . Emitted-light color decision portion, 120 . . . Login controller, 122 . . . Select image generating unit, 124 . . . Camera image generating unit, 126 . . . Login processing unit, 128 . . . Sign-in processing unit, 140 . . . Biometric authentication portion, 142 . . . Login user storage portion, 144 . . . User monitor portion, 150 . . . Registered user information holding section, 200 . . . Focus frame, 202, 204 . . . Face frames

INDUSTRIAL APPLICABILITY

The present invention is applicable to the fields of information processing technologies.

The invention claimed is:

1. An information processing apparatus comprising:
a communication section configured to receive a connection request from a device to connect the device with the information processing apparatus;
an image capture section configured to capture a taken image from an imaging apparatus;
a registered user information holding section configured to hold biometric information of a user registered in the information processing apparatus;
a biometric authentication portion configured to compare biometric information of a user included in the taken image with biometric information held in the registered user information holding section to determine whether the imaged user is a user registered in the information processing apparatus; and
a login controller configured, after the imaged user is found to be a user registered in the information processing apparatus, to execute login processing of the user,
wherein the login controller stores information for identifying a device included in the taken image and information for identifying a user of the device into a storage portion by relating these pieces of information with each other.

2. The information processing apparatus according to claim 1, further comprising
an emitted-light color decision portion configured to decide an emitted light color for a device having a light emitting block,
wherein the login controller stores emitted light color information determined by the emitted-light color decision portion into the storage portion as information for identifying a device included in the taken image.

3. The information processing apparatus according to claim 1, further comprising a monitor portion configured to monitor a relation between information for identifying a device included in the taken image and information for identifying the user.

4. The information processing apparatus according to claim 3, wherein, if the relation is found wrong, the monitor portion executes notification of a result of this determination.

5. The information processing apparatus according to claim 1, wherein the login controller generates a select image in which pieces of information for identifying a plurality of registered users are arranged in a row, the pieces of information being held in the registered user information holding section, and, in the generated select image, the user found to be a registered user by the biometric authentication portion is selected only by operating an enter key of a device.

6. An information processing apparatus comprising:
an image capture section configured to capture a taken image from an imaging apparatus;

a registered user information holding section configured to hold information of a user registered in the information processing apparatus;

a receiving section configured to receive a login request from a user;

a first image generating block configured, if the receiving section receives a first login request, to display, on a display as a first login screen, a select image that allows the user to select information for identifying himself from among pieces of information for identifying a plurality of registered users arranged in a row, the pieces of information being held in the registered user information holding section; and a second image generating block configured, if the receiving section receives a second login request, to display the taken image on the display as a second login screen.

7. A non-transitory, computer readable storage medium containing a computer program, the computer program, when executed by a computer, causing the computer to carry out actions, comprising:

connecting a device with the computer upon receiving a connection request from the device;

capturing a taken image from an imaging apparatus;

comparing biometric information of a user included in the taken image with biometric information held in a holding section configured to hold biometric information of a user registered in the computer to determine whether the imaged user is a user registered in the computer; and executing, after the imaged user is found to be a user registered in the computer, executing login processing of the user;

executing login processing including storing information for identifying a device included in the taken image and information for identifying a user of the device into a storage portion by relating these pieces of information with each other.

8. A non-transitory, computer readable storage medium containing a computer program, the computer program, when executed by a computer, causing the computer to carry out actions, comprising:

capturing a taken image from an imaging apparatus;

receiving a login request from a user;

displaying, if a first login request is received, on a display as a first login screen, a select image that allows the user to select information for identifying himself from among pieces of information for identifying a plurality of registered users arranged in a row, the pieces of information being held in a holding section configured to hold information of a user registered in the computer; and displaying, if a second login request is received, the taken image on the display as a second login screen.

* * * * *